US00PP14902P3

(12) United States Plant Patent
Kordes

(10) Patent No.: US PP14,902 P3
(45) Date of Patent: Jun. 15, 2004

(54) MINIATURE ROSE PLANT NAMED 'KORBLTYP'

(50) Latin Name: *Rosa hybrida*
Varietal Denomination: KORbltyp

(75) Inventor: Tim-Hermann Kordes, Offenseth-Sparrieshoop (DE)

(73) Assignee: W. Kordes Sohne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 21 days.

(21) Appl. No.: 10/078,624

(22) Filed: Feb. 19, 2002

(65) Prior Publication Data

US 2003/0159186 P1 Aug. 21, 2003

(51) Int. Cl.[7] ..... A01H 5/00
(52) U.S. Cl. ..... Plt./116
(58) Field of Search ..... Plt./116, 117, 121

*Primary Examiner*—Howard J. Locker
(74) *Attorney, Agent, or Firm*—Webb Ziesenheim Logsdon Orkin & Hanson, P.C.

(57) ABSTRACT

A new miniature rose plant which has abundant flowers with a red-purple center and light pink outer petals and attractive glossy dark foliage. The variety successfully propagates from softwood cuttings and is suitable for year round production in commercial glasshouses as a flowering pot plant.

3 Drawing Sheets

BACKGROUND OF THE NEW PLANT

The present invention constitutes a new and distinct variety of miniature rose plant named 'KORbltyp' which was developed by artificially pollinating an unnamed seedling (unpatented) with an unnamed seedling (unpatented).

The objective of the hybridization of this rose variety for commercial greenhouse culture was to create a new and distinct variety with:

1. Uniform and abundant flowers with good keepability;
2. Attractive long lasting foliage and compact growth;
3. Year round flowering under glasshouse conditions;
4. Suitability for production from softwood cuttings in pots; and
5. Durable flowers and foliage which make the variety suitable for distribution in the floral industry.

This combination of qualities was not present in previously available commercial cultivars of this type and distinguish 'KORbltyp' from other varieties.

The two parents were crossed in the summer of 1999 and the resulting seed was sown in December 1999 in a controlled glasshouse environment. The seeds from hybridization were planted in a controlled environment in Klein Offenseth, Sparrieshoop, Germany and evaluations were conducted on the resulting plants. The instant cultivar originated as a single plant from the stated cross.

Asexual reproduction of 'KORbltyp' by softwood cuttings was first done in Denmark and later in California in controlled greenhouse environments. The characteristics of the new variety remain true to type through successive propagations.

The new rose variety may be distinguished from its seed parent, an unnamed breeding seedling, by the following combination of characteristics:

1. 'KORbltyp' has big double flowers, while the seed parent has small double flowers.
2. 'KORbltyp' has flowers with a red-purple center and light pink outer petals, while the seed parent has dark purple petals.

The new variety may be distinguished from its pollen parent, an unnamed breeding seedling by the following combination of characteristics:

1. 'KORbltyp' has bigger flowers and foliage as compared to the pollen parent.
2. 'KORbltyp' has flowers with a red-purple center and light pink outer petals, while the pollen parent has dark red petals.

The new variety differs from 'KORmisso', U.S. Plant Pat. No. 11,264, as set forth in Table 1:

TABLE 1

| | 'KORbltyp' | 'KORmisso' |
|---|---|---|
| Petal color, upper surface | Red-Purple Group 66C | Red Group 54B |
| Petal color, reverse surface | Red-Purple Group 66D | Red Group 54B |
| Petal count | 40–45 petals | 50–60 petals |

DESCRIPTION OF THE DRAWINGS

The accompanying color illustrations show as true as is reasonably to obtain in color photographs of this type, the typical characteristics of the buds, flowers, leaves, stems of 'KORbltyp'.

In photo sheet #1.

Figures 1, 2, 3, 4, 5, 6, 7, 8, 9:
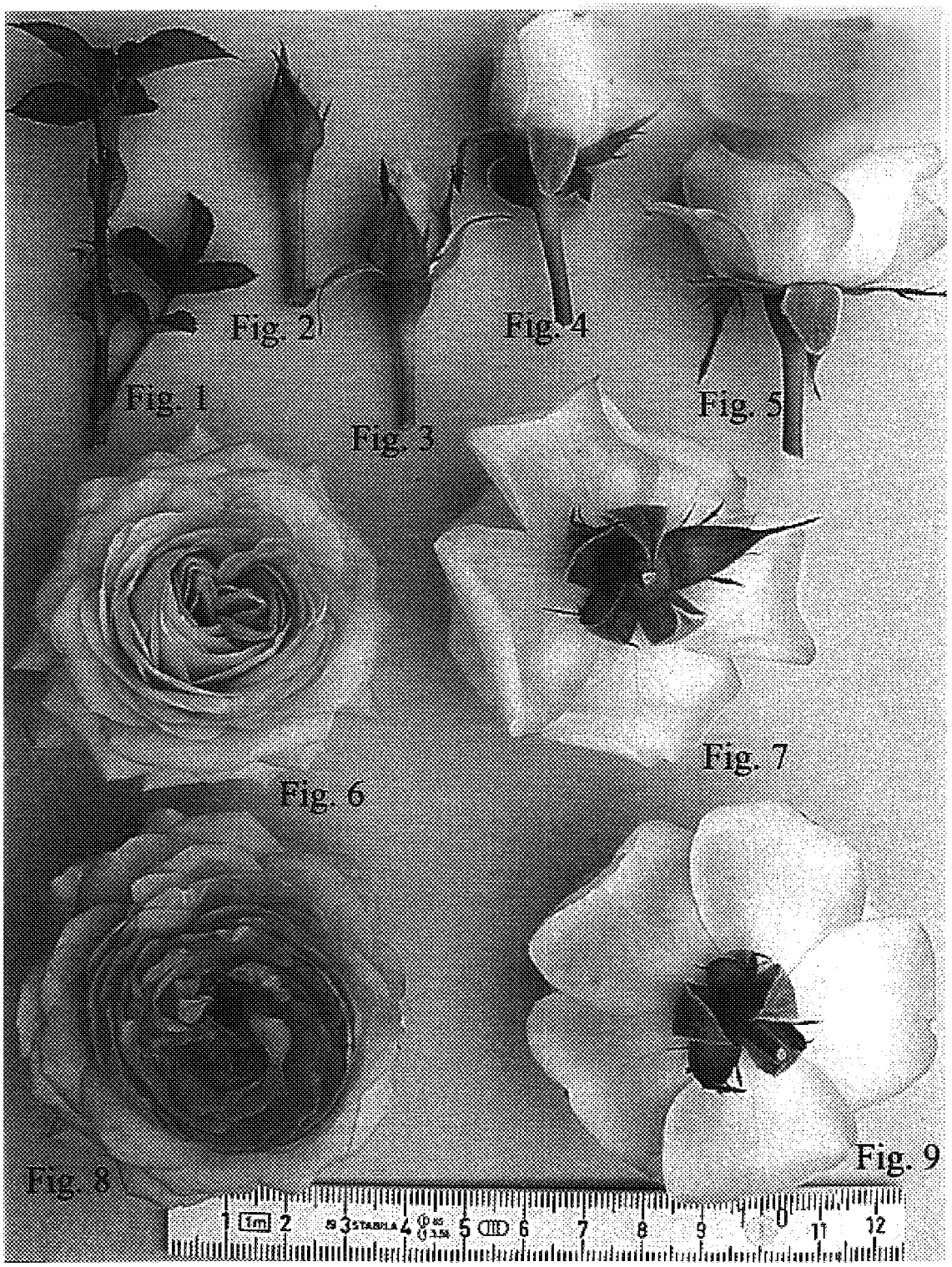
FIG. 1 shows a young shoot.
FIG. 2 shows a bud before opening of the sepals.
FIG. 3 shows a bud at the opening of the sepals.
FIG. 4 shows a bud at the opening of the petals.
FIG. 5 shows a flower during the course of opening.
FIG. 6 shows an open flower, obverse plan view.
FIG. 7 shows an open flower, reverse plan view.
FIG. 8 shows a fully open flower, obverse plan view.
FIG. 9 shows a fully open flower, reverse plan view.
Figures 10, 11, 12, 13, 14, 14A:
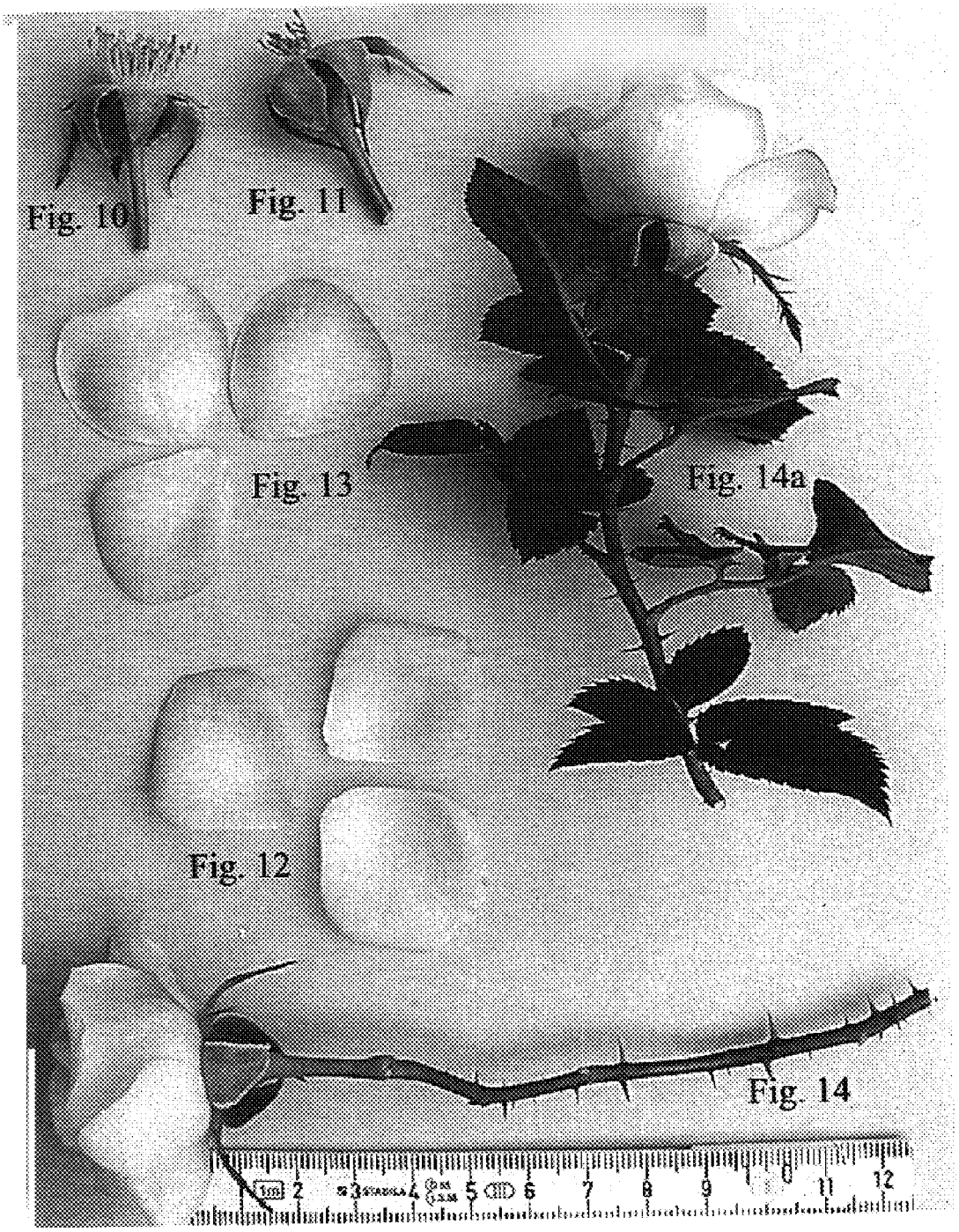

In photo sheet #2:

FIG. 10 shows a receptacle with stamens and pistils.
FIG. 11 shows a receptacle with pistils and stamens removed.

FIG. 12 shows detached flower petals, outer surface.

FIG. 13 shows detached flower petals, inner surface.

FIG. 14 shows a bare stem exhibiting thorns and flower attachment.

In photo sheet #3:

FIG. 14*a* shows a stem exhibiting leaves and flower attachment.

Figures 15, 16, 17, 18:
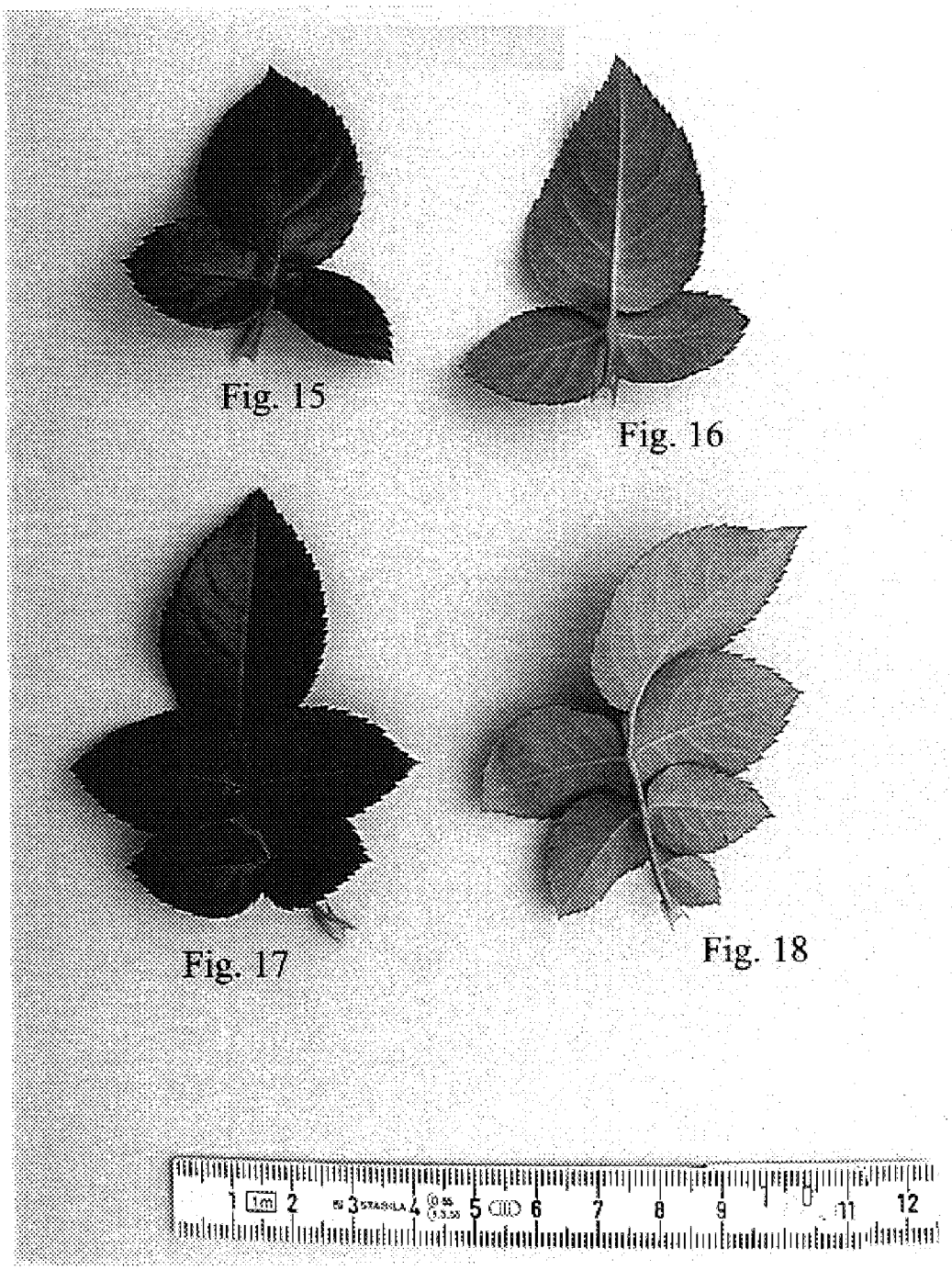

FIG. 15 shows three leaflets, upper side.

FIG. 16 shows three leaflets, under side.

FIG. 17 shows five leaflets, upper side.

FIG. 18 shows five leaflets, under side.

DESCRIPTION OF THE NEW PLANT

The following is a detailed description of 'KORbltyp', as observed in its growth in greenhouses in Fraugde, Denmark and greenhouses in Santa Barbara, Calif. both at 20–25° C.

Descriptions were made from plants 11 to 13 weeks old after propagation produced in a pot treated with growth regulators normally used in the greenhouse production process. The growth regulator Paclobutrazol was applied at 15–30 ppm weekly beginning at a plant age of 8 weeks. The peduncle lengths mentioned may actually be shorter and the foliage color several shades darker than on untreated specimens. Color references are made using The Royal Horticultural Society (London, England) Colour Chart, 1995, except where common terms of color are used.

THE PLANT

Classification:
- *Botanical.*—*Rosa hybrida.*
- *Commercial.*—Miniature.

Plant growth: Moderately vigorous. Grows compact upright to bushy. When grown as 10 cm pot plant, the average height of the plant itself is 18–20 cm, and average width is 20 cm. When grown as a 15 cm pot plant, the average height of the plant itself is 22–27 cm, and average width is 30 cm. Production time is generally 11–13 weeks depending on average temperature, light level, and cultural practices.

Stem:
- *Color.*—Young wood: Green Group 138B, with intonations of Greyed-Purple Group 185A. Older wood: Green Group 138A.
- *Surface.*—Young wood: Smooth, with many prickles. Older wood: Smooth, with many prickles.
- *Stem diameter.*—2–3 mm.
- *Stem length.*—15 cm in a 10 cm pot; 20 cm in a 15 cm pot.
- *Internode length.*—15–20 mm.
- *Number of internodes.*—6–7.
- *Thorns.*—Incidence: Many prickles on both young and older wood. Size: 4–6 mm. Color: Red-Purple Group 61C. Shape: Triangular and elongated.

FOLIAGE

Arrangement: Alternate, compound with 3–7 leaflets per leaf, generally symmetrical, abundant, and flat in aspect. Stipules at petiole base.

Quantity of leaves: 6–7 per lateral branch.

Leaf size for an average leaf having 5 leaflets:
- *Length.*—65–70 mm.
- *Width.*—45–50 mm.

Petioles:
- *Color.*—Green Group 138A with intonations of Greyed-Purple Group 185A.
- *Margin.*—Stipitate glands present.
- *Length.*—10 mm average for a 5 leaflet leaf.
- *Diameter.*—About 1 mm.
- *Prickles.*—Few, average 2–3.

Stipules:
- *Size.*—5–7 mm.
- *Surface.*—Smooth with stipitate glands.
- *Color.*—Green Group 138A with intonations of Greyed-Purple Group 185A.

Rachis:
- *Color.*—Green Group 138C with intonations of Greyed-Purple Group 185A.
- *Margins.*—Stipitate glands present.
- *Length.*—10–25 mm.

Leaflets:
- *Margin.*—Serrated.
- *Serration.*—Single to double.
- *Shape.*—Ovate with acute apex and obtuse base.
- *Texture.*—Smooth.
- *Appearance.*—Glossy.
- *Size.*—Length: 15–45 mm. Width: 10–30 mm.
- *Color.*—Young foliage: Upper surface: Green Group 137C with intonations of Greyed-Purple Group 185A. Lower surface: Green Group 137D with intonations of Greyed-Purple Group 185A. Mature foliage: Upper surface: Green Group 136A. Lower surface: Yellow-Green Group 147B.

INFLORESCENSE

Blooming habit: Recurrent.

Number of flowers: Generally 1 bud per flowering stem.

Peduncle:
- *Color.*—Green Group 138A with intonations of Red-Purple Group 61C.
- *Texture.*—Smooth.
- *Length.*—20–25 mm.
- *Form.*—Upright.

Receptacle:
- *Surface.*—Smooth.
- *Shape.*—Funnel-shaped.
- *Size.*—Height: 5 mm. Width: 7 mm.
- *Color.*—Green Group 138A, with intonations of Red-Purple Group 61C.

Sepals:
- *Quantity.*—5.
- *Shape.*—Narrowly ovate with acute tip.
- *Texture.*—Slightly pubescent.
- *Margin.*—Foliaceous appendages on three of the five sepals.
- *Appearance.*—Dull.
- *Color.*—Upper surface: Green Group 138A. Reverse surface: Green Group 138A with intonations of Greyed-Purple Group 185A.

Buds:
- *Size when just opening.*—Length: 18–20 mm. Width: 15–17 mm.
- *Shape.*—Ovoid.
- *Color.*—Green-White Group 157B with intonations of Red-Purple Group 58B at one-fourth opened.

Flower:
- *Duration.*—As a pot plant, flowers last from 10–16 days.
- *Fragrance.*—None.
- *Size.*—55–60 mm in diameter.
- *Form.*—Shape of flower when viewed from the side. Upon opening: Ovoid. Open flower: Cupped to flat.

*Color.*—Petals, upon opening: Upper surface: Red-Purple Group 66C; basal petal spots Yellow-Orange Group 14C. Reverse surface: Red-Purple Group 66D; basal petal spots Yellow Group 11A. Petals, after opening: Upper surface: Red-Purple Group 68B. Reverse surface: Red-Purple Group 68B.

*Basal petal spots.*—Size: 8–10 mm. Color: Green-White Group 157D.

*General tonality of open flower.*—Red-Purple Group 68B on third day fading to Red-Purple Group 69B.

Petals:

*Petal reflex.*—Outermost petals reflex backward upon opening. Fully open, all petals reflex backward.

*Texture.*—Smooth and satiny.

*Petal edge.*—Uniform.

*Petal count.*—Approximately 40–45 per flower.

*Petal size.*—Length: 30 mm. Width: 30 mm.

*Shape.*—Outer petals: Ovate to round. Inner petals: Ovate to round.

*Petaloids.*—Usually none.

Reproductive organs:

*Stamens.*—Number: Approximately 25 per flower. Pollen: Color: Yellow-Orange Group 22A. Amount: Average.

*Anthers.*—Size: 1–2 mm. Color: Yellow-Orange Group 22A. Shape: Oblong. Number: 80–85.

*Filaments.*—Size: 3–4 mm. Color: Yellow-Orange Group 22A.

Pistils:

*Number.*—Approximately 30–35 per flower.

*Stigmas.*—Location: Superior in location to anthers. Color: Greyed-Orange Group 164C.

*Styles.*—Color: Greyed-White Group 157D. Length: 2–3 mm.

GROWTH

Vegetation: Dense.

Blooming: Abundant.

Aptitude to bear fruit: Poor.

Resistance to diseases: Above average resistance to mildew and Botrytis under normal growing conditions in Fraugde, Denmark and Santa Barbara, Calif.

Hips/seeds: Unknown, the plant has never been grown to the stage of seed development due to the fact that the variety is developed for use as a flowering potted plant only.

Winter hardiness and drought/heat tolerance: This variety is a potted flowering plant developed for indoor use only and, due to lack of hardiness, it is not suitable to be used under outdoor conditions.

I claim:

1. A new and distinct variety of rose plant substantially as shown and described.

* * * * *